US009066516B2

(12) United States Patent
Koivunen et al.

(10) Patent No.: US 9,066,516 B2
(45) Date of Patent: Jun. 30, 2015

(54) USES OF THAXTOMIN AND THAXTOMIN COMPOSITIONS AS HERBICIDES

(71) Applicant: Marrone Bio Innovations, Inc., Davis, CA (US)

(72) Inventors: Marja Koivunen, Davis, CA (US); Pamela Marrone, Davis, CA (US); Louis Boddy, Davis, CA (US)

(73) Assignee: Marrone Bio Innovations, Inc., Davis, CA (US)

(*) Notice: Subject to any disclaimer, the term of this patent is extended or adjusted under 35 U.S.C. 154(b) by 102 days.

(21) Appl. No.: 13/841,606

(22) Filed: Mar. 15, 2013

(65) Prior Publication Data

US 2013/0217573 A1 Aug. 22, 2013

Related U.S. Application Data

(63) Continuation-in-part of application No. 13/553,677, filed on Jul. 19, 2012, now Pat. No. 8,822,381, which is a continuation-in-part of application No. 12/650,315, filed on Dec. 30, 2009, now Pat. No. 8,476,195.

(60) Provisional application No. 61/261,504, filed on Nov. 16, 2009, provisional application No. 61/142,179, filed on Dec. 31, 2008.

(51) Int. Cl.
*A01N 43/60* (2006.01)
*A01N 43/70* (2006.01)

(52) U.S. Cl.
CPC ..................................... *A01N 43/60* (2013.01)

(58) Field of Classification Search
CPC .................................................... A01N 43/60
USPC ........................................................ 504/117
See application file for complete search history.

(56) References Cited

U.S. PATENT DOCUMENTS

| 2,891,855 | A | * | 6/1959 | Hans Gysin et al. | ......... 504/168 |
|---|---|---|---|---|---|
| 4,309,208 | A | | 1/1982 | Takematsu et al. | |
| 4,990,178 | A | | 2/1991 | Haneishi et al. | |
| 7,393,812 | B2 | | 7/2008 | Gerwick, III et al. | |
| 7,504,244 | B2 | | 3/2009 | Szabo et al. | |
| 7,989,393 | B2 | | 8/2011 | Kang et al. | |
| 8,476,195 | B2 | | 7/2013 | Koivunen et al. | |
| 2004/0102320 | A1 | | 5/2004 | Grimm | |
| 2004/0192551 | A1 | | 9/2004 | Bessette | |
| 2008/0248956 | A1 | | 10/2008 | Kang et al. | |
| 2009/0099022 | A1 | | 4/2009 | Fernandez et al. | |
| 2010/0167930 | A1 | * | 7/2010 | Koivunen et al. | ............ 504/136 |
| 2010/0267560 | A1 | | 10/2010 | Leep et al. | |
| 2013/0190175 | A1 | | 7/2013 | Koivunen et al. | |
| 2013/0288896 | A1 | | 10/2013 | Koivunen et al. | |
| 2013/0296169 | A1 | | 11/2013 | Koivunen et al. | |

FOREIGN PATENT DOCUMENTS

| WO | WO 2008124675 | 10/2008 |
|---|---|---|
| WO | WO 2013066894 | 10/2008 |
| WO | WO 2010066677 | 6/2010 |
| WO | WO 2010078452 | 7/2010 |

OTHER PUBLICATIONS

International Search Report and Written Opinion for PCT App. No. PCT/IB2013/002214 dated Jan. 28, 2014 (14 pages).
U.S. Appl. No. 13/840,975, Not yet published, Huazhang Huang et al.
Beausejour, "Production of Thaxtomin A by *Streptomyces scabies* Strains in Plant Extract Containing Media," *Can. J. Microbiol.* 45:764-768 (1999).
Duke, "Natural Products as Sources of Herbicides: Current Status and Future Trends," *Weed Res.* 40:99-111 (2000).
Duke, "United States Department of Agriculture-Agricultural Research Service Research on Natural Products for Pest Management," *Pest Management Sci.* 59:708-717 (2003).
Duval, "Thaxtomin A Induces Programmed Cell Death in *Arabidopsis thaliana* Suspension-Cultured Cells," *Planta* 222:820-831 (2006).
Fry, "Thaxtomin A: Evidence for a Plant Cell Wall Target," *Physiolog. Molec. Plant Pathol.* 60:1-8 (2002).
Healy, "The txtAB Genes of the Plant Pathogen *Streptomyces acidiscabies* Encode a Peptide Synthetase Required for Phytotoxin Thaxtomin A Production and Pathogenicity," *Molec. Microbiol.* 38:794-804 (2000).
Hiltunen, "Influence of Thaxtomins in Different Combinations and Concentrations on Growth of Micropropagated Potato Shoot Cultures," *J. Agric. Food Chem.* 54:3372-3379 (2006).
Hoagland, "Microbial Allelochemicals and Pathogens as Bioherbicidal Agents," *Weed Technol.* 15:835-857 (2001).
Johnson, "Plant-Pathogenic *Streptomyces* Species Produce Nitric Oxide Synthase-Derived Nitric Acid in Response to Host Signals," *Chemistry & Biology* 15:43-50 (2007).
King, "Isolation and Characterization of Phytotoxins Associated with *Streptomyces scabies*," *J. Chem. Soc. Chem. Commun.* 13:849-850 (1989).
King, "Chemistry of Phytotoxins Associated with *Streptomyces scabies*, the Causal Organism of Potato Common Scab," *J. Agric. Food Chem.* 40:834-837 (1992).
King, "Herbicidal Properties of the Thaxtomin Group of Phytotoxins," *J. Agric. Food Chem.* 49:2298-2301 (2001).
King, "More Chemistry of the Thaxtomin Phytotoxins," *Phytochemistry* 64:1091-1096 (2003).
Koivunen, "Evaluation of a New Natural Product Herbicide for Rice Weed Control," *Proceedings of the California Weed Science Society* 61:113 (2009).

(Continued)

*Primary Examiner* — Abigail Fisher
*Assistant Examiner* — Andriae M Holt
(74) *Attorney, Agent, or Firm* — Ying-Horng Liu (57) ABSTRACT

There is a need for a selective, low-risk herbicide that can be used to control weeds in cereal cultures and turf. The present invention discloses that a bacterial secondary metabolite, thaxtomin and optionally another herbicide is an effective herbicide on broadleaved, sedge and grass weeds. Thaxtomin A and structurally similar compounds can be used as natural herbicides to control the germination and growth of weeds in cereal, turf grass, Timothy grass and pasture grass cultures with no phytotoxicity to these crops. As a natural, non-toxic compound, thaxtomin can be used as a safe alternative for weed control in both conventional and organic farming and gardening systems.

10 Claims, 2 Drawing Sheets

(56) References Cited

OTHER PUBLICATIONS

Loria, "Differential Production of Thaxtomins by Pathogenic *Streptomyces* Species in Vitro," *Phytopathology* 85:537-541 (1995).
Scheible, "An Arabidopsis Mutant Resistant to Thaxtomin A, a Cellulose Synthesis Inhibitor from *Streptomyces* Species," *The Plant Cell* 15:1781-1794 (2003).
Taylor, "Casoron, A New Aquatic Herbicide," *Hyacinth Control Journal/J. of Aquatic Plant Management* 5:20-21 (1966), available at www.apms.org/japm/vol05/v5p20.pdf.
Examination Report for NZ App. No. 596336 (Aug. 23, 2012).
Examination Report for NZ App. No. 598365 (Aug. 23, 2012).
Extended Search Report for EP App. No. 098371743 (May 12, 2012).
Extended Search Report for EP App. No. 10765219.0 (Jul. 23, 2012).
International Search Report and Written Opinion for PCT App No. PCT/US2009/069856 (Aug. 13, 2010).
International Search Report and Written Opinion for PCT App. No. PCT/US2010/031317 (Nov. 11, 2010).
International Preliminary Report on Patentability for PCT App. No. PCT/US2010/031317 (Oct. 18, 2011).
Office Action (Final Rejection) for U.S. Appl. No. 12/761,382 (Dec. 22, 2011).
Office Action (Non-Final Rejection) for U.S. Appl. No. 12/761,382 (Oct. 5, 2012).

* cited by examiner

USES OF THAXTOMIN AND THAXTOMIN COMPOSITIONS AS HERBICIDES

PRIORITY CLAIM

This application is a continuation-in-part of application Ser. No. 13/533,677 filed Jul. 19, 2012, which is a continuation-in-part of application Ser. No. 12/650,315, the contents of which are incorporated herein by reference. Application Ser. No. 12/650,315 claims priority from U.S. application Ser. Nos. 61/142179, filed Dec. 31, 2008 and 61/261504 filed Nov. 16, 2009 under 35 USC 119(e), in which the contents of both are incorporated herein by reference and also claims priority from Taiwan Patent application no. 098144895, filed Dec. 25, 2009 under 35 USC 119(a)-(d), the contents of which are also incorporated herein by reference.

REFERENCE TO GOVERNMENT GRANT

This invention was supported in part by funds obtained from the U.S. Government (USDA SBIR Grant Number: 2011-33610-30455). The U.S. Government may have certain rights in the invention.

FIELD OF THE INVENTION

This invention relates to compositions and methods for controlling the germination and growth of broadleaf, sedge and grass weeds using compounds comprising thaxtomin, a cyclic dipeptide produced by *Streptomyces* sp., as an active ingredient.

BACKGROUND OF THE INVENTION

Natural products are substances produced by microbes, plants, and other organisms. Microbial natural products offer an abundant source of chemical diversity, and there is a long history of utilizing natural products for pharmaceutical purposes. However, secondary metabolites produced by microbes can also be successfully used for weed and pest control in agricultural applications.

Thaxtomins (4-nitroindol-3-yl-containing 2,5-dioxopiperazines) are a family of dipeptide phytotoxins produced by plant-pathogenic *Streptomyces* sp. (*S. scabies, S. acidiscabies*) that cause scab diseases in potato (*Solanum tuberosum*) (King, Lawrence et al. 1992). Toxin production occurs in diseased tissue and can also be elicited in vitro in an optimal growth medium containing oat bran (Loria, Bukhalid et al. 1995; Beauséjour, Goyer et al. 1999). King and her coworkers (King, Lawrence et al. 2001) demonstrated that all plant pathogenic species in the *Streptomyces* family produce one or more thaxtomins with herbicidal activity. Hiltunen et al. (Hiltunen, Laakso et al. 2006) purified four thaxtomin analogs (thaxtomin A, thaxtomin A ortho isomer, thaxtomin B and thaxtomin D) from cultures of *S. scabies* and *S. turbidiscabies* and showed that all four compounds induced similar symptoms of reduced shoot and root growth, root swelling, (at 10-200 ppb) and necrosis (at 200-1000 ppb) on micropropagated in vitro cultures of potato. In addition, thaxtomins applied in combinations, showed additive effects, but no synergism (Hiltunen, Laakso et al. 2006). According to Duke et al. (Duke, Baerson et al. 2003), both thaxtomin A (FIG. 1) and thaxtomin D have marked activity as pre and post emergent, non-systemic herbicides, and concentrations of less than 1 uM of thaxtomin A causes cell swelling, necrosis and growth inhibition in mono and dicotyledonous seedlings (Healy, Wach et al. 2000). Thaxtomin has been evaluated as an herbicide by Dow Agro Sciences, Inc., and while active, it lacked systemic action (King, Lawrence et al. 2001). The presence of the nitro group in the indole ring required for an L,L-configuration of the diketopiperazine appears to be the minimal requirement for phytotoxicity. The position of the nitro group in the indole ring is very site specific, and the phenyl portion of the phenylalanine plays a necessary role in structural requirements of phytotoxicity (King, Lawrence et al. 1989; King, Lawrence et al. 1992; King, Lawrence et al. 2003). The herbicidal mode of action is based on disruption of cell wall synthesis (Fry and Loria 2002), with inhibition of cellulose biosynthesis being the main target (King et al., 2001; Duval et al., 2005; Johnson et al. 2007). Recently, Kang et al. (Kang, Semones et al. 2008) have described the use of thaxtomin and thaxtomin compositions as algaecides to control algae in water environments.

SUMMARY OF THE INVENTION

The present invention discloses the use of thaxtomin as a pre or post-emergence herbicide against most common weeds in the cereal, pasture grass, Timothy grasses and turf grass, residential gardens, vineyards, orchards and park growth systems. A "growth system" may be any ecosystem for growing cereal, pasture grass, Timothy grass and turf grass. For example, a "cereal growth system" may be a cereal growth culture or may be a field containing planted cereal crops or cereal seeds. Similarly, a "turf grass growth system" may be a turf grass growth culture or may be a field, lawn or golf course containing planted turf grass or turf grass seeds. It can serve as a safer alternative to synthetic herbicides now on the market. A primary object of the invention is to provide novel herbicidal compositions against both broadleaf, sedge and grassy weeds, that contains thaxtomin as an active ingredient. Another object is to provide a safe, non-toxic herbicidal composition that does not harm cereal crops, pasture grass, Timothy grass or turf grass and a method that will not harm the environment.

The above and other objects are accomplished by the present invention which is directed to herbicidal compositions containing at least one herbicidal agent, e.g., thaxtomin with optionally certain carriers to control the growth and germination of weeds in the cereal growth system and/or turf grass growth system and/or Timothy grass growth system and/or pasture grass growth system. In particular, the invention is further directed to an herbicidal composition for use in modulating the germination and growth of monocotyledonous and/or dicotyledenous and/or sedge weeds in a cereal growth system. In a particular embodiment, the cereal growth system is a non-rice cereal growth system comprising at least one herbicide in which said herbicide is thaxtomin The compositions of the present invention may further comprise a carrier and/or diluent. In a particular embodiment, the composition is an aqueous composition. In another particular embodiment, the thaxtomin in the composition is dissolved in a diluent comprising an organic solvent such as ethanol, isopropanol, or an aliphatic ketone such as acetone, methyl ethyl ketone, methyl isobutyl ketone.

In a related aspect, the invention is directed to the use of at least one herbicidal agent, e.g., thaxtomin, in the formulation of an herbicide for modulating monocotyledonous and/or dicotyledenous and/or sedge weeds in a cereal growth system, e.g., a non-rice cereal growth system. Similarly, the invention is directed to the use of at least one herbicidal agent in formulation of an herbicide for modulating monocotyledonous and/or dicotyledenous and/or sedge weeds in a turf grass growth system and/or Timothy grass growth system and/or pasture grass growth system, wherein at least one herbicidal agent is thaxtomin.

The compositions of the present invention may comprise in addition to thaxtomin, at least one or more herbicides. Thus the invention may comprise a thaxtomin and a chemical herbicide and/or bioherbicide. Compositions comprising thaxtomin and at least a second herbicide may be used in cereal growth systems (e.g., wheat, triticale, barley, oats, rye, corn, sorghum, sugarcane, rice or millet) and/or turf grass growth systems and/or Timothy grass growth systems and/or pasture grass growth systems and/or residential gardens, vineyards, orchards and park systems and/or aquatic systems. In a particular embodiment these compositions may be used to modulate growth of broadleaf, sedge and grassy weeds, The compositions may also be used to modulate growth of aquatic weeds which include but are not limited to *Ammania* sp., Alisma plantago-aquatica, *Cyperus* sp., *Leptochloa* sp.

Given that the invention is directed to the use of thaxtomin as a pre- or post-emergence herbicide, the invention is directed to a method for selectively modulating germination and growth of monocotyledonous, dicotyledonous and sedge weeds in a cereal crop growth system. In a particular embodiment, the cereal growth system is a non-rice cereal crop growth system comprising applying to said weeds or soil in said cereal crop growing system at least one herbicidal agent, wherein said herbicidal agent is thaxtomin, in an amount of effective to modulate germination and growth of said weeds but not modulate growth of cereal crop in said cereal crop growth system. The cereal crop may include but is not limited to corn, wheat, triticale, barley, rye, oats, sorghum, sugarcane, and millet. The invention is further directed to a method for modulating germination and growth of monocotyledonous, dicotyledonous and sedge weeds in a turf, pasture and/or Timothy grass growth system comprising applying to said weeds or soil in said turf grass growing system at least one herbicidal agent, wherein said herbicidal agent is thaxtomin, in an amount of effective to modulate growth of said weeds but not modulate germination and growth of turf grass in said turf grass growth system, pasture grass in said pasture grass growth system and/or Timothy grass in said Timothy grass growth system.

As noted above, the method of the present invention may also involve the use of at least a second herbicidal agent. The two herbicidal agents may be applied together in one formulation or separately in two formulations. Thus, provided is a combination comprising thaxtomin and a second herbicidal agent. The combination may be a synergistic combination. In a particular embodiment, the E/Ee ratio is at least about 1.2, 1.5, 1.7, 1.9, 2.0, 2.5, or higher.

Control of weeds can be achieved by using thaxtomin A in a tank mix or rotation with other herbicidally active compounds known to have good activity against grass weeds but no or low phytotoxicity against cereal crops and/or turf grass and/or, pasture grass and/or Timothy grasses. In particular, the invention relates to a method for modulating growth of monocotyledonous, dicotyledonous and sedge weeds comprising applying to said weeds an amount of thaxtomin and amount of at least a second herbicidal agent to modulate growth of said weeds. The two herbicidal agents may be applied together in one formulation or separately in two formulations. The thaxtomin and second herbicidal agent may be applied in a cereal growth system (e.g., wheat, triticale, barley, oats, rye, corn, sorghum, sugarcane, rice or millet) and/or turf grass growth system and/or pasture grass growth system and/or Timothy grass growth system.

DETAILED DESCRIPTION OF THE INVENTION

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

Thaxtomin utilized in this invention may be derived in fermentation of the following actinomycetes cultures: *S. scabies*—ATCC 49173, *S. acidiscabies*—ATCC 49003 and BL37-EQ-010—or it can be purchased from commercial sources.

The thaxtomin utilized in the invention include but are not limited to agents described as cyclic dipeptides having the basic structure cyclo-(L-4-nitrotryptophyl-L-phenylalanyl). In embodiments, suitable diketopiperazne moieties may be N-methylated, and include congeners carrying phenylalanyl alpha andring-carbon hydroxyl groups. The chemical in a particular embodiment comprises:

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, and combinations thereof.

Figure 1:
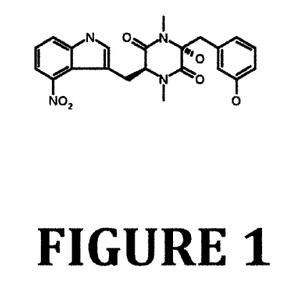
FIG. 1 shows the structure of Thaxtomin A.

Non limiting examples of suitable thaxtomin is for use in accordance with the present invention include but are not limited to thaxtomin A, thaxtomin A ortho isomer, thaxtomin B, thaxtomin C, hydroxythaxtomin C, thaxtomin A p-isomer, hydroxythaxtomin A and des-N-methylthaxtomin C and derivatives of any of these (See FIG. 1).

Compositions

The compositions of the present invention may be sprayed on the plant or applied to soil. Particular embodiments are described in the Examples, infra. These compositions may be in the form of dust, coarse dust, micro granules, granules, wettable powder, emulsifiable concentrate, liquid preparation, suspension concentrate, water degradable granules or oil suspension.

The compositions of the invention do comprise a carrier and/or diluent. The term, 'carrier' as used herein means an inert, organic or inorganic material, with which the active ingredient is mixed or formulated to facilitate its application to plant or other object to be treated, or its storage, transport and/or handling. Examples of diluents or carriers for the pre- and post-emergence herbicides include, but are not limited to, water, milk, ethanol, mineral oil, glycerol.

The compositions of the present invention may comprise at least two herbicidal agents. One herbicidal agent is thaxtomin set forth above. It may be present in one embodiment thaxtomin is present in an amount ranging from about 0.01 to about 5.0 mg/mL. The other herbicidal agent may be a bioherbicide and/or a chemical herbicide. The bioherbicide may be derived from a plant, or may be a microbial bioherbicide. In particular, the bioherbicide derived from a plant may be derived from pepper (e.g., sarmentine) or may be a plant essential oil (e.g., lemongrass oil). The microbial bioherbicide may be derived from bacteria (e.g. *Streptomyces* sp., *Burkholderia* sp., particularly *Burkholderia* sp. or fractions, supernatant, filtrate, or compounds derived therefrom which disclosed in WO/2011/106491 and PCT/US12/50807, the contents of which are incorporated herein by reference or fungus. The bioherbicide may be selected from the group consisting of clove, cinnamon, lemongrass, citrus oils, orange peel oil, bialaphos, cornexistin, AAL-toxin, leptospermone and other triketones (such as 2-(2-nitro-4-trifluoromethyl-benzoyl)cyclohexane-1,3-dione, flavesone, grandiflorone, etc.), sarmentine or sarmentine analog, momilactone B, sorgoleone, ascaulatoxin, manuka oil, *Phoma macrostoma*, d-limonene, m-tyrosine, tentoxin, nethylated seed oil, chelated iron, acetic acid and ascaulatoxin aglycone. In a particular embodiment, the composition may comprise thaxtomin, lemongrass oil and optionally a surfactant and/or vegetable oil. In another embodiment, the composition may comprise thaxtomin, sarmentine and optionally a nonionic surfactant and/or vegetable oil. In another particular embodiment, the composition may comprise thaxtomin, bialaphos (also known as bialafos) and optionally a nonionic surfactant and/or vegetable oil. The bioherbicide such as lemongrass oil, bialaphos (bialfos), manuka oil, sarmentine, sarmentine analog, *Burkholderia* species may be present in an amount ranging from about 0.01 mg/mL to about 100 mg/mL and more preferably between about 0.025 mg/mL to about 50 mg/mL The chemical herbicide may be selected from the group consisting of 24-D, Acetochlor, Acifluorfen, Amicarbazone, Anilofos, Asulam, Atrazine, Bensulfuron, Bentazone, Byspiribac-sodium, Carfentrazone, Chlorthiamid, Clomazone, Cyhalofop-butyl, Dicamba, Diclofop. Dithiopyr, Diuron, EPTC, Fenoxaprop, Flumioxazin, Fluridone, Fluroxypyr, Fomesafen, Glufosinate, Glyphosate, Halosulfuron, Imazethapyr, Indazifam, Isoxaben, Linuron, MCPA (4-chloro-2-methylphenoxy acetic acid), MCPP, Mesotrione, Metolachlor, Metribuzin, MSMA, Napropamide, Nicosulfuron, Norflurazon, Oleic acid, Oryzalin, Oxadiazon, Oxyfluorfen, Quinclorac, Pelargonic acid, Pendimethalin, Penoxsulam, Picloram, Propanil, Pyrithrobac-sodium, Rimsulfuron, Saflufenacil, Sethoxydim, Simazine, Sulcotrione, Thiazopyr, Thiencarbazone, Thiobencarb, Triclopyr, Trifluralin, Trioxysulfuron-sodium.

The chemical herbicide such as pendimethalin or clomazone, atrazine, oryzalin, trifluralin and metolachlor may be present in a pre-emergent weed control application in an amount ranging from about 0.01 mg/mL to about 50 mg/mL and a chemical herbicide such as clomazone, cyhalofop, oryzalin, S-metolachlor, bispyribac-sodium, glyophosate, glufosinate, mesotione, penoxsulam, carfentrazone, quinclorac, triclopyr-ester, trioxysulfuron-sodium, thiobencarb, propanil, 2,4-D, dicamba in a pre or post-emergent application from about 0.1 mg/mL to about 60 g a.i./mL or 0.03 kg a.i./ha to 5.6 kg a.i./ha. The composition may further comprise an adjuvant which may be vegetable oil comprising ethyl oleate, polyethylene dialkyl ester and ethoxylated nonylphenol. The composition may additionally comprise a surfactant to be used for the purpose of emulsification, dispersion, wetting, spreading, integration, disintegration control, stabilization of active ingredients, improvement of fluidity or rust inhibition. The choice of dispersing and emulsifying agents, such as non-ionic, anionic, amphoteric and cationic dispersing and emulsifying agents, and the amount employed is determined by the nature of the composition and the ability of the agent to facilitate the dispersion of the herbicidal compositions of the present invention.

For post-emergent formulations, the formulation components used may contain smectite clays, attapulgite clays and similar swelling clays, thickeners such as xanthan gums, gum Arabic and other polysaccharide thickeners as well as dispersion stabilizers such as nonionic surfactants (for example polyoxyethylene (20) monolaurate or polysorbate 60 POE (20) sorbitan monostearate, ethylene glycol monostearate). The concentration of the clays may vary between about 0-2.5% w/w of the total formulation, the polysaccharide thickeners may range between about 0-0.5% w/w of the total formulation and the surfactants may range from about 0-5% w/w of the total formulation.

Uses

The compounds, combinations and compositions set forth herein may be used to modulate the emergene and/or growth of various weeds and can thus be used in pre-emergent and post-emergent applications. Said weeds may include but are not limited to *Echinochloa phyllopogon, Echinochloa colona, Echinochloa oryzoides, Echinochloa crus-galli, Schoenoplectus* spp., *Heteranthera* spp., *Monochoria* spp., *Bacopa* spp., *Sagittaria* spp., *Oryza punctata* and *Oryza sativa* (weedy). The application we filed also includes the following targets: *Chenopodium* sp. (e.g., *Chenopodium album, Chenopodium murale*), *Abutilon* sp. (e.g., *Abutilon theophrasti*), *Helianthus* sp. (e.g., *Helianthus annuus*), *Ambrosia* sp. (e.g., *Ambrosia artemesifolia, Ambrosia trifida*), *Amaranthus* sp. (e.g., *Amaranthus retroflexus, Amaranthus palmeri, Amaranthus rudis, Amaranthus spinosus, Amaranthus tuberculatus*), *Convolvulus* sp. (e.g., *Convolvulus arvensis*), *Brassica* sp. (e.g., *Brassica kaber*), *Taraxacum* sp. (e.g., *Taraxacum officinale*), *Solanum* sp. (e.g., *Solanum nigrum, Solanum elaeagnifolium, Solanum physalifolium, Solanum ptycanthum*), *Malva* sp. (e.g., *Malva neglecta*), *Setaria* sp. (e.g., *Setaria lutescens*), *Bromus* sp. (e.g., *Bromus tectorum, Bromus diandrus, Bromus hordeaceus*), *Poa* sp. (e.g., *Poa annua, Poa pratensis*), *Lolium* sp. (e.g., *Lolium perenne, Lolium rigidum, Lolium multiflorum* L. var. Pace), *Festuca* sp. (e.g., *Festuca arundinaceae, Festuca rubra*), *Echinochloa* sp. (e.g., *Echinochloa crus-galli, Echinochloa colona*), and particularly, Lambsquarter—*Chenopodium album*, Redroot Pigweed—*Amaranthus retroflexus*, Wild Mustard—*Brassica kaber*, Dandelion—*Taraxacum officinale*, and Black Nightshade—*Solanum nigrum*, *Oxalis* sp. (e.g., *Oxalis stricta, Oxalis pes-caprae, Oxalis corniculata*); *Cyperus* sp. (e.g., *Cyperus difformis*); *Conyza* sp. (e.g., *Conyza canadensis, Conyza sumatrensis, Conyza bonariensis*); *Sagina* sp. (e.g., *Sagina procumbens*); *Veronica* sp. (e.g., *Veronica hederafolia*), *Stellaria* sp. (e.g., *Stellaria media*), *Rorippa* sp. (e.g., *Rorippa islandica*), *Senecio* sp. (e.g., *Senecio vulgaris*), *Lamium* sp. (e.g., *Lamium amplexicaule*), *Digitaria* sp. (e.g., *Digitaria sanguinalis, Digitaria ischaemum*), *Galium* sp. (e.g., *Galium aparine*), *Galinsoga* sp. (e.g., *Galinsoga aristatula*), *Cardamine* sp. (e.g., *Cardamine flexuosa, Cardamine hirsuta*), *Kochia* sp. (e.g., *Kochia scoparia*), *Eleusine* sp. (e.g., *Eleusine indica*), *Portulaca* sp. (e.g., *Portulaca oleraceae*), *Plantago* sp. (e.g., *Plantago lanceolata*), *Euphorbia* sp. (e.g., *Euphornia supina, Euphorbia maculate, Euphorbia esula, Euphorbia prostrata*), *Erodium* sp. (e.g., *Erodium cicutarium*), *Sonchus* sp., (e.g., *Sonchus oleraceus*), *Lactuca* sp. (e.g., *Lactuca serriola*), *Capsella* sp. (e.g., *Capsella bursa-pastoris*), *Leptochloa* sp. (e.g., *Leptochloa fascicularis, Leptochloa virgata*), *Raphanus* sp. (e.g., *Raphanus raphanistrum*), *Calandrinia* sp. (e.g., *Calandrinia ciliata*), *Paspalum* sp. (e.g., *Paspalum dilatatum*), *Gnaphalium* sp., *Cynodon* sp. (e.g., *Cynodon dactylon, Cynodon hirsutus*), *Polygonum* sp. (e.g., *Polygonum arenastrum, Polygonum lapathofolium*), *Avena fatua, Hordeum* sp. (e.g., *Hordeum leporinum*), *Urtica* sp. (e.g., *Urtica urens*), *Tribulus terrestris, Sisymbrium* sp. (e.g., *Sisymbrium irio*), *Cenchrus* sp., *Salsola* sp. (e.g., *Salsola tragus, Salsola kali*), *Amsinckia* sp. (e.g., *Amsinckia lycopsoides*), *Ipomoea* sp., *Claytonia perfoliata, Polypogon* sp. (e.g., *Polypogon monspeliensis*), *Xanthium* sp., *Hypochaeris radicata, Physalis* sp., *Eragrostis* sp., *Verbascum* sp., *Chamomilla suaveolens, Centaurea* sp. (e.g., *Centaurea solstitialis*), *Epilobium brachycarpum, Panicum* sp. (e.g., *Panicum capilare, Panicum dichotomiflorum*), *Rumex acetosella, Eclipta* sp. (e.g., *Eclipta alba, Eclipta prostrata*), *Ludwigia* sp., *Urochloa* sp. (e.g. *Urochloa platyphylla, Urochloa panicoides*), *Leersia* sp., *Sesbania* sp. (*Sesbania herbacea*), *Rotala* sp., *Ammania* sp., *Alternathera philoxeroides, Commelina* sp., *Sorghum halepense, Parthenium hysterophorus, Chloris truncata*

EXAMPLES

The composition and method of the present invention will be further illustrated in the following, non-limiting Examples. The examples are illustrative of various embodiments only and do not limit the claimed invention regarding the materials, conditions, weight ratios, process parameters and the like recited herein.

Example 1

In a pot study test in greenhouse conditions, 6-inch corn plants (*Zea mays* var. Sunglow) were sprayed with increasing concentrations of thaxtomin A mixed in a carrier 4% ethanol, 0.02% polysorbate 60 POE (20) sorbitan monostearate solution. The spraying solutions contained 0.125, 0.25, 0.5 and 1.0 mg thaxtomin A/mL, and the plants are sprayed until total coverage. Each treatment was done in three replicates, and a control solution consists of water with 4% ethanol and 0.02% polysorbate 60 POE (20) sorbitan monostearate as a surfactant. Prior to and after treatments, plants are grown in a greenhouse under artificial lights (12-h light/dark cycle) at 25° C.

Plants are evaluated in one-week intervals starting at 7 days after treatment. The final evaluation is done three weeks after treatment, at which time point, no phytotoxicity is observed in any of the test plants even at the highest thaxtomin A concentration.

Example 2

A pot study is conducted to test the phytotoxicity of thaxtomin A on corn (*Zea mays* var. Early Sunglow) and wheat (*Triticum aestivum* var. PR1404). To confirm the activity on broadleaf weeds, pigweed (*Amaranthus* sp.) is planted in the same pot with either three corn or five wheat seeds, and sprayed simultaneously with the cereal test plants. The less than 3-inch tall plants grown under growth lights (12-h light/12-h dark) at 28° C. are sprayed with thaxtomin A solutions derived from a liquid culture of *S. acidiscabies* containing 0.5, and 1.0 mg thaxtomin A per mL of solvent (4% ethanol and 0.2% non-ionic surfactant). A solution of 4% ethanol +0.2% non-ionic surfactant without thaxtomin A is used as a control treatment. Each treatment is conducted in three replicates. Treated plants are kept at 28° C. under growth lights and observed at three time points—7, 14 and 21 days after treatment—for visual symptoms of phytotoxicity on corn and wheat and % control of pigweed.

At each time point, no symptoms of phytotoxicity are observed in the cereal plants treated with thaxtomin A. The highest concentration of thaxtomin A (1.0 mg/mL) results in a complete control of pigweed grown in the same pots with corn and wheat.

Example 3

To test the phytotoxicity of thaxtomin A on sorghum plants, five seeds of sorghum (*Sorghum bicolor*) are planted in each 4"×4" plastic pot filled with soil. Plants were grown under optimal conditions in a greenhouse before and after treatment with solutions containing 0.5 and 1.0 mg thaxtomin A/mL. At the time of the treatment, the plants are about 3 inches tall. Each treatment is applied in three replicates, and a control treatment included plants treated with just the carrier (4% EtOH, 0.02% polysorbate 60 POE (20) sorbitan monostearate). Evaluations for phytotoxicity are performed at 7-day intervals starting one week after treatment. The last evaluation is performed three weeks after the treatment at which point, no phytotoxicity is observed in the treated plants in any treatment concentration.

Example 4

A strain of *S. acidiscabies* (ATCC-49003) is grown in oat bran broth for 5 days (25° C., 200 rpm). The whole cell broth with thaxtomin A is extracted using XAD resin. The dried crude extract was resuspended in 4% ethanol and 0.02% non-ionic surfactant at a concentration of 10 mg/mL, and the solutions with two different concentrations of thaxtomin A (0.5 and 1.0 mg/mL) are tested the following broadleaf weed species:

Lambsquarter—*Chenopodium album*
Velvetleaf—*Abutilon theophrasti*
Sunflower—*Helianthus annuus*
Ragweed, Common—*Ambrosia artemesifolia*
Pigweed, Redroot—*Amaranthus retroflexus*
Bindweed, Common—*Convolvulus arvensis*
Mustard, Wild—*Brassica kaber*
Dandelion—*Taraxacum officinale*
Nightshade, Black—*Solanum nigrum*
Mallow, Common—*Malva neglecta*
and on the following grass weed species:

Foxtail—*Setaria lutescens*
Brome, Downy—*Bromus tectorum*
Bluegrass, Annual—*Poa annua*
Bluegrass, Kentucky—*Poa pratensis*
Ryegrass, Perennial—(*Lolium perenne* L. var. Pace)
Fescue, Tall—(*Festuca arundinaceae Schreb*. var. Aztec II, Anthem II, LS 1100)
Barnyard Grass—*Echinochloa crus-galli*

All plant species are tested in 4"×4" plastic pots in three replicates. The untreated control plants are sprayed with the carrier solution (4% Ethanol, 0.02% glycosperse) and the positive control plants with Roundup at a rate corresponding to 1 fl. oz/acre. Treated plants are kept in a greenhouse under 12 h light/12 h dark conditions. Data for broadleaf species from weekly evaluations are presented in Table 1.

TABLE 1

Weed control efficacy of a *S. acidiscabies* extract containing thaxtomin A on different weed species. Rating scale: 0 - no control, 1 - 10% control, 2 - 25% control, 3 - 50% control, 4 - 75% control, 5 - 100% control.

| Weed species | UTC | | | THAXTOMIN SOLUTION 0.5 mg/mL | | | THAXTOMIN SOLUTION 1.0 mg/mL | | |
|---|---|---|---|---|---|---|---|---|---|
|  | 7 DAYS | 14 DAYS | 21 DAYS | 7 DAYS | 14 DAYS | 21 DAYS | 7 DAYS | 14 DAYS | 21 DAYS |
| Dandelion | 0.0 | 0.0 | 0.0 | 2.0 | 2.3 | 4.0 | 2.0 | 2.0 | 3.7 |
| Nightshade | 0.0 | 0.0 | 0.0 | 2.7 | 2.2 | 2.3 | 2.7 | 2.0 | 2.3 |
| Lambsquarter | 0.0 | 0.0 | 0.0 | 2.0 | 2.0 | 2.0 | 2.0 | 2.0 | 2.0 |
| Ragweed | 0.0 | 0.0 | 0.0 | 1.0 | 0.5 | 0.0 | 1.0 | 0.5 | 0.0 |
| Velvetleaf | 0.0 | 0.0 | 0.0 | 1.7 | 1.0 | 1.0 | 2.0 | 1.0 | 0.3 |
| Bindweed | 0.0 | 0.0 | 0.0 | 1.0 | 1.0 | 0.0 | 1.2 | 1.0 | 0.0 |
| Mustard | 0.0 | 0.0 | 0.0 | 3.3 | 4.0 | 4.5 | 3.5 | 2.8 | 3.5 |
| Sunflower | 0.0 | 0.0 | 0.0 | 1.0 | 2.0 | 0.5 | 1.0 | 1.7 | 0.5 |
| Mallow | 0.0 | 0.0 | 0.0 | 1.0 | 1.0 | 1.0 | 1.2 | 1.0 | 1.0 |
| Pigweed | 0.0 | 0.0 | 0.0 | 3.5 | 4.0 | 4.0 | 4.2 | 3.0 | 3.7 |

The extract from a bacterial culture of *S. acidiscabies* with a thaxtomin A concentration of 0.5 mg/mL or higher showed good efficacy (>50%) against at least three of the most common broadleaf weed species (dandelion, mustard and pigweed) in both cereal and turf growing systems. Control of some weeds such as Black nightshade and Common lambsquarter was not complete but thaxtomin A even at the lower concentration (0.5 mg/mL) results in severe stunting of these weeds. In this same study, no adverse effects are observed in grass species treated with either 0.5 or 1.0 mg/mL thaxtomin A. In all tested grass species, no phytotoxic effects were visible at even the higher thaxtomin A concentration.

Example 5

The combined effect of thaxtomin A and two commercial herbicides (Bipyribac-sodium formulated as Regiment and Lemongrass oil formulated as GreenMatch EX) on small-flower umbrella sedge and watergrass is tested in a field study using small (1-sq foot) plots. All single product treatments and tank mix combinations were sprayed at 57 gal per acre. Evaluation of % control was done 14 days after treatment and the results are presented in Table 2 below. Means in each column marked with the same letter in Table 2 are not statistically different from each other at p<0.05

According to the results, lemongrass oil at 1.25% weight does not improve the efficacy of thaxtomin A (at 0.25 mg/mL) on sedge but it significantly increases the efficacy on grass weeds such as watergrass (field test) and sprangletop (greenhouse test).

TABLE 2

Effect of thaxtomin A alone and in combination with bispyribac-sodium and lemongrass oil on two rice weeds, small-flower umbrella sedge and watergrass.

| Treatment | Sedge control (%) | Watergrass control (%) |
|---|---|---|
| Thaxtomin 0.25 mg/mL | 95a | 5d |
| Thaxtomin 0.5 mg/mL | 100a | 5d |
| Bispyribac-sodium (12 g/acre) (12 g/acre) | 87.5a | 32.5a |
| Bispyribac-sodium ½ (6 g/acre) | 47.5c | 15c |
| Bispyribac-sodium ½ + Thaxtomin 0.5 mg/mL | 67.5b | 25ab |
| Bispyribac-sodium ½ + | 55bc | 7.5c |

TABLE 2-continued

Effect of thaxtomin A alone and in combination with bispyribac-sodium and lemongrass oil on two rice weeds, small-flower umbrella sedge and watergrass.

| Treatment | Sedge control (%) | Watergrass control (%) |
|---|---|---|
| Thaxtomin 0.25 mg/mL | | |
| Lemongrass oil 5% | 15d | 10c |
| Lemongrass oil 2.5% | 12.5d | 10c |
| Lemongrass oil 1.25% | 20d | 5d |
| Lemongrass oil 1.25% + Thax 0.25 mg/mL | 100a | 10c |
| Lemongrass oil 1.25% + Thaxtomin 0.5 mg/mL | 100a | 20b |

According to the results, lemongrass oil at 1.25% does not improve the efficacy of thaxtomin A (at 0.25 mg/mL) on sedge but it significantly increases the efficacy on grass weeds such as watergrass (field test) and sprangletop. Thaxtomin A (at 0.5 mg/mL) improves the efficacy of an ALS inhibitor, bipyribac sodium; used at half label rate on both sedge and grasses.

Example 6

The efficacy of thaxtomin A derived from a liquid culture of *S. acidiscabies* is tested in a field study on rice using 4.9 sq-ft plots surrounded by a metal ring. Treatments with either thaxtomin A or thaxtomin A in combination with lemongrass oil (formulated as GreenMatch EX) or cyhalofop (formulated as Clincher CA) were done using a hand-held sprayer with a water volume corresponding to 57 gallons per acre. Rice (variety M209) was grown until maturity and harvested by hand for yield and weed count assessment. Results of yield (kg/ha), and numbers of redstem, small-flower umbrella sedge, and sprangletop in each plot are presented in Table 3 below.

TABLE 3

Effect of thaxtomin A alone and in combination with lemongrass oil and cyhalofop on rice yield and weed control.

| Treatment | Yield (kg/ha) | # of redstem | # of sedge | # of sprangletop |
|---|---|---|---|---|
| 1 | 7516b | 10.3 | 0.8a | 86.0a |
| 2 | 7876b | 0.5b | 1.0a | 76.0a |
| 3 | 9054ab | 0.3b | 0.5a | 69.3a |
| 4 | 11296a | 12.8a | 0.5a | 4.0b |

1. UTC;
2. Thaxtomin A (180 g/acre);
3. Lemongrass oil 1.25% + thaxtomin A (90 g/acre);
4. Cyhalofop (half label rate; 52 g/acre) + thaxtomin A (90 g/acre) + veg oil 2.5%
Means in each column marked with the same letter are not statistically different from each other at p < 0.05.

Results indicate that thaxtomin at 180 g/acre significantly reduced the number of sedges but had no effect on sprangletop or yield. When used at half rate (thaxtomin A 90 g/acre), a combination with lemongrass oil had better effect on sedges than a combination with cyhalofop (used at half label rate 52 g/acre). Good grass weed (sprangletop) control is achieved when thaxtomin (90 g/acre) is combined with cyhalofop at half the label rate—this combination also improves the yield significantly.

Example 7

Cyhalofop (2-[4-(4-cyano-2-fluorophenoxy)phenoxy] propanoic acid, butyl ester) is also mixed together with adjuvant containing ethyl oleate, polyethylene dialky ester and ethoxylated nonylphenol (2.5% v/v) and increasing concentrations of thaxtomin A (purified from the ATCC strain 49003) at concentrations 0.1, 0.2 and 0.4 mg/ml. The concentrations of the 2-[4-(4-cyano-fluorophenoxy)phenoxy]propanoic acid, butyl ester before dilution are 29.6% (2.38 lb/gal) and 21.7% (2 lb/gal), respectively. The effect of these mixtures on the growth of common water plantain, red stem, smallflower sedge and sprangletop is determined in the greenhouse. Similarly, rice plants of variety M104 are grown and tested for phytotoxic effects, and all plants are evaluated 7, 14, and 21 days after treatment. Results of from the study with cyhalofop formulated as Clincher CA at the 21-day evaluation point are presented in Table 4 below.

TABLE 4

Effect of thaxtomin A alone and with cyhalofop on rice yield and weed control

| Cyhalofop (6.5 oz/acre) + Thaxtomin A (mg/mL) | Redstem % control | Waterplantain % control | Sedge % control | Sprangletop % control |
|---|---|---|---|---|
| UTC | 0 | 0 | 0 | 0 |
| 0 - no thx A | 75 | 8 | 0 | 90 |
| 0.1 | 100 | 85 | 87 | 100 |
| 0.2 | 97 | 87 | 88 | 100 |
| 0.4 | 100 | 85 | 100 | 100 |

As a conclusion, Clincher CA (29.6% cyhalofop by weight) applied at half label rate (6.5 oz/acre) has good efficacy against grass weeds—not so good on broadleaves and poor on sedges. A combination of Clincher CA (cyhalofop) and thaxtomin A provides good control of all rice weeds tested in this study. Efficacy of thaxtomin A against grass weeds is substantially improved if combined with Clincher. Combination of thaxtomin A with Clincher CA did not cause phytotoxicity on rice at any tested concentration.

Example 8

Penoxsulam(2-(2,2-difluoroethoxy)-N-(5,8-dimethoxy[1,2,4]triazolo[1,5c]pyrimidin-2-yl)-6-trifluoromethyl)benzenesulfonamide) is mixed together with adjuvant containing ethyl oleate, polyethylene dialky ester and ethoxylated nonylphenol (2.5% v/v) and increasing concentrations of thaxtomin A (purified from the ATCC strain 49003) at concentrations 0.1, 0.2 and 0.4 mg/ml. The concentrations of the 2-[4-(4-cyano-fluorophenoxy)phenoxy]propanoic acid, butyl ester or 2-(2,2-difluoroethoxy)-N-(5,8-dimethoxy[1,2,4]triazolo[1,5c]pyrimidin-2-yl)-6-trifluoromethyl)benzenesulfonamide before dilution are 29.6% (2.38 lb/gal) and 21.7% (2 lb/gal), respectively. The effect of these mixtures on the growth of common water plantain, red stem, smallflower sedge and sprangletop is determined in the greenhouse. Similarly, rice plants of variety M104 are grown and tested for phytotoxic effects, and all plants are evaluated 7, 14, and 21 days after treatment.

Example 9

A strain of S. acidiscabies was grown in oat bran broth for 5 days (25° C., 200 rpm). The whole cell broth was extracted using XAD resin, and the dried crude extract was resuspended in 4% ethanol and 0.2% non-ionic surfactant at a concentration of 10 mg/mL. The diluted extracts containing 0.2 and 0.4 mg thaxtomin A per mL were tested on three weed species (redstem; *Ammania* spp., smallflower umbrella sedge; *Cyperus difformis* and sprangletop: *Leptochloa uninervia*). Other treatments included sarmentine at 2.5 and 5.0 mg/mL, and a combination treatment containing 0.2 mg thaxtomin A and 2.5 mg sarmentine per mL. Each treatment was applied in three replicates. Treated plants were kept in a greenhouse under 12 h light/12 h dark conditions. Results from an evaluation performed 25 days after treatment are presented in Table 5.

TABLE 5

Efficacy of herbicidal treatments using thaxtomin A (0.2 and 0.4 mg/mL) or sarmentine (2.5 or 5.0 mg/mL) alone or in combination (0.2 + 2.5 mg/mL) to control broadleaf, sedge and grass weeds in a greenhouse study.

| Treatment | Control of redstem (%) | Control of sedge (%) | Control of sprangletop (%) |
|---|---|---|---|
| UTC | 0a | 0a | 0a |
| Thaxtomin A 0.2 mg/mL | 5.0b | 48.3b | 8.3ab |
| Thaxtomin A 0.4 mg/mL | 11.7c* | 91.7d | 10.0b |
| Thaxtomin 0.2 + Sarmentine 2.5 mg/mL | 11.7c* | 61.7c | 73.3c |
| Sarmentine 2.5 mg/mL | 0a | 8.3a | 80.0c |
| Sarmentine 5.0 mg/mL | 2.5ab | 6.7a | 92.3d |

*stunted. In a column, Means followed by the same letter are not statistically different from each other at p < 0.05.

Thaxtomin A at the highest concentration of 0.4 mg/mL provides excellent control of sedge but poor control of the grass weed (sprangletop). When combined with sarmentine, the efficacy against grass weeds improves significantly. Also, efficacy against sedge is improved with the combination treatment compared with the single application of thaxtomin A alone at the corresponding concentration. In this study, the control of the broadleaf weed (redstem) is poor with all treatments.

Example 10

Bialaphos is produced by bacteria *Streptomecyes* spp. and its synthesized active ingredient glufosinate is marketed as Rely® 200 (Bayer CropScience, Research Triangle Park, NC). Bialaphos has a non-selective property and inhibits the activity of glutamine synthetase, an enzyme involved in the synthesis of the amino acid glutamine.

The MBI-005 and bialaphos were prepared at various concentrations either as single ingredients or in combination with bialaphos. The treatments were applied at approximately ⅔ ml per replicate with a hand-help spray nozzle to barnyard grass or sedge. There were 3 replicates per treatment which were randomized after spray and were kept in a greenhouse at 25° C. for evaluation of phytotoxicity (% control).

When MBI-005 was mixed with bialaphos, the efficacy was increased several times more than when they were used alone (Table 6, 7, and 8). At higher rates of the mixtures, 100% control was achieved (Table 8). Synergy was observed when bialaphos at 0.178 mg/mL was mixed with MBI-005 at 0.25 mg/mL, and about 42% efficacy was achieved when the rate of bialaphos was increased close to 1.0 mg/mL from 10% control with bialaphos alone (Table 7).

TABLE 6

Effects of bialaphos, MBI-005 (thaxtomin A), and the combinations of bialaphos with MBI-005 in controlling barnyard grass.

| Treatment | Bialaphos (mg/mL) | MBI-005 (mg/L) | % Control (14 days) | E/Ee[#] |
|---|---|---|---|---|
| Untreated Control (deionized water) | | | 0.0 a* | |
| Bialaphos | 0.089 | | 0.0 a | |
| Bialaphos | 0.178 | | 0.0 a | |
| Bialaphos | 0.356 | | 0.0 a | |
| Bialaphos | 0.534 | | 0.0 a | |
| Bialaphos | 0.712 | | 0.0 a | |
| Bialaphos | 0.890 | | 1.3 ab | |
| Bialaphos | 1.068 | | 5.0 abc | |
| MBI-005 (thaxtomin A) | | 0.25 | 1.3 ab | |
| Bialaphos + MBI-005 | 0.089 | 0.25 | 1.3 ab | 1.0 |
| Bialaphos + MBI-005 | 0.178 | 0.25 | 3.8 abc | 3.0 |
| Bialaphos + MBI-005 | 0.356 | 0.25 | 11.9 c | 9.5 |
| Bialaphos + MBI-005 | 0.534 | 0.25 | 29.4 d | 23.5 |
| Bialaphos + MBI-005 | 0.712 | 0.25 | 34.4 d | 27.5 |
| Bialaphos + MBI-005 | 0.890 | 0.25 | 59.4 e | 23.9 |
| Bialaphos + MBI-005 | 1.068 | 0.25 | 62.5 e | 10.1 |

*Treatment means in each column marked with the same letter are not statistically different at LSD at p = 0.05 level.
[#]Synergy is calculated from Colby's formula (Colby, 1967. Weeds 15:20-22): Ee = X + Y − (XY/100) (Where E is the observed efficacy of product A + B, Ee is expected efficacy of A + B, and X and Y are the efficacy of product A or B when used alone. If E/Ee <1 the combination is antagonistic; if E/Ee = 1 the combination is additive; if E/Ee >1 the combination is synergistic).

TABLE 7

Effects of bialaphos, MBI-005 (thaxtomin A), and the combinations of bialaphos with MBI-005 in controlling barnyard grass.

| Treatment | Bialaphos (mg/mL) | MBI-005/011 (mg/mL) | % Control (14 days) | E/Ee |
|---|---|---|---|---|
| Untreated Control (deionized water) | | | 0.0 a* | |
| Bialaphos | 0.18 | | 6.7 bc | |
| Bialaphos | 0.53 | | 3.3 ab | |
| Bialaphos | 1.07 | | 10.0 c | |
| MBI-005 (thaxtomin A) | | 0.25 | 6.7 bc | |
| Bialaphos + MBI-005 | 0.18 | 0.25 | 5.0 abc | 0.4 |
| Bialaphos + MBI-005 | 0.53 | 0.25 | 25.0 d | 2.6 |
| Bialaphos + MBI-005 | 1.07 | 0.25 | 41.7 e | 2.6 |

*Treatment means in each column marked with the same letter are not statistically different with LSD test at p = 0.05 level

TABLE 8

Effects of bialaphos, MBI-005 (thaxtomin A), and the combinations of bialaphos with MBI-005 or MBI-011 in controlling barnyard grass.

| Treatment | Bialaphos (mg/mL) | MBI-005 (mg/mL) | % Control (7 days) | % Control (14 days) | E/Ee (7 days) |
|---|---|---|---|---|---|
| Untreated Control (deionized water) | | | 0.0 a* | 0.0 a | |
| Bialaphos | 1.1 | | 5.0 ab | 3.7 a | |
| Bialaphos | 1.4 | | 10.8 b | 23.3 b | |
| Bialaphos | 1.8 | | 62.5 c | 66.7 c | |
| MBI-005 (thaxtomin A) | | 0.38 | 6.7 ab | 21.7 b | |
| Bialaphos + MBI-005 | 1.1 | 0.38 | 87.5 d | 100.0 d | 7.7 |
| Bialaphos + MBI-005 | 1.4 | 0.38 | 87.5 d | 100.0 d | 5.2 |
| Bialaphos + MBI-005 | 1.8 | 0.38 | 87.5 d | 100.0 d | 1.3 |

*Treatment means in each column marked with the same letter are not statistically different with LSD at p = 0.05 level.

Example 11

The test species barnyard grass, ragweed, sedge, and broad-leaf mustard were used for the valuation of synergy between MBI-005 and the rice herbicides clomazone, penoxsulam, cyhalofop, fenoxaprop-p-ethyl, bispyribac-sodium, thiobencarb, and propanil.

The common turf weeds dandelion and plantain were used in testing for synergy between MBI-005 and 2, 4- or dicamba, two common turf herbicides.

Three other herbicides commonly used for field crops, glyphosate, glufosinate, synthetic version of bialaphos, and mesotrione were also tested for synergy with MBI-005 on crabgrass and ragweed.

There were 3 replicates per treatment which were sprayed with approximately ⅔ ml per replicate. The treatments were completely randomized and kept in a greenhouse at 25° C. The efficacy was rated at 7 and 14 days post treatment. The results are shown in Table 9 to 11. For barnyard grass control, MBI-005 had synergistic effects when combined with clomazone, (penoxsulam, bispyribac-sodium, thiobencarb, and propanil (Table 9). MBI-005 had additive effects when combined with cyhalofop, and fenoxaprop-p-ethyl (Table 10).

MBI-005 showed great synergy with glyphosate for controlling ragweed and also showed synergy with both turf herbicides. The synergistic effect of MBI-005 with glufosinate (synthetic bialaphos) (Table 11) on crabgrass was likely less since the rate of MBI-005 was too low.

TABLE 9

Summary of synergistic or additive effects between MBI-005 (thaxtomin A) and commercial products for rice weed control. The data are means of percentage control of three replicates 14 days post treatment.

| Active Ingredient | Test Species | Product Rate (mg/mL) | MBI-005 Rate (mg/mL) | % Control Product | % Control MBI-005 | % Control Product + MBI-005 | E/Ee |
|---|---|---|---|---|---|---|---|
| clomazone | Barnyard grass | 0.513 | 0.25 | 37.5 | 28.3 | 91.7 | 1.7 |
| | Mustard | 0.513 | 0.25 | 25.0 | 58.3 | 70.8 | 1.0 |
| | Sedge | 0.501 | 0.02 | 0.0 | 37.5 | 50.0 | 1.3 |
| penoxsulam | Barnyard grass | 0.051 | 0.125 | 25.0 | 17.5 | 75.0 | 2.0 |
| | Sedge | 0.047 | 0.01 | 66.7 | 20.0 | 87.5 | 1.2 |
| cyhalofop | Mustard | 0.051 | 0.125 | 11.7 | 13.3 | 15.0 | 0.6 |
| | Sedge | 1.176 | 0.01 | 3.3 | 20.0 | 8.3 | 0.4 |
| fenoxaprop-p-ethyl | Barnyard grass | 0.006 | 0.25 | 91.7 | 66.7 | 87.5 | 0.9 |
| | Mustard | 0.006 | 0.125 | 0.0 | 45.8 | 33.3 | 0.7 |
| | Sedge | 0.116 | 0.02 | 0.0 | 70.8 | 66.7 | 0.9 |
| bispyribac-sodium | Barnyard grass | 0.032 | 0.125 | 0.0 | 3.3 | 62.5 | 18.8 |
| | Mustard | 0.0216 | 0.25 | 53.3 | 37.5 | 95.8 | 1.4 |
| | Ragweed | 0.0216 | 0.125 | 5.0 | 23.3 | 50.0 | 1.8 |
| thiobencarb | Barnyard grass | 1.743 | 0.25 | 41.7 | 41.7 | 79.2 | 1.2 |
| | Mustard | 1.743 | 0.125 | 10.0 | 54.2 | 54.2 | 0.9 |
| | Sedge | 3.15 | 0.02 | 58.3 | 37.5 | 70.8 | 1.0 |
| propanil | Barnyard grass | 0.365 | 0.125 | 32.5 | 10.0 | 79.2 | 2.0 |
| | Mustard | 0.036 | 0.25 | 1.67 | 58.3 | 50.0 | 0.9 |

TABLE 10

Summary of synergistic or additive effects between MBI-005 (thaxtomin A) and commercial products for turf weed control. The data are means of percentage control of three replicates 14 days post treatment.

| Active Ingredient | Weed Species | Product Rate (mg/mL) | MBI-005 Rate (mg/mL) | % Control Product | % Control MBI-005 | % Control Product + MBI-005 | E/Ee |
|---|---|---|---|---|---|---|---|
| 2, 4-D | Dandelion | 0.176 | 0.1 | 25.0 | 20.0 | 91.7 | 2.3 |
| | Plantain | 2.340 | 0.24 | 50.0 | 25.0 | 83.3 | 1.3 |
| dicamba | Dandelion | 0.121 | 0.1 | 45.8 | 20.0 | 75.0 | 1.3 |
| | Plantain | 6.025 | 0.12 | 50.0 | 10.0 | 79.2 | 1.4 |

TABLE 11

Summary of synergistic or additive effects between MBI-005 (thaxtomin A) and commercial products with broad spectrum. The data are means of percentage control of three replicates 14 days post treatment.

| Active Ingredient | Weed Species | Product Rate (mg/mL) | MBI-005 Rate (mg/mL) | % Control Product | % Control MBI-005 | % Control Product + MBI-005 | E/Ee |
|---|---|---|---|---|---|---|---|
| glyphosate | Crabgrass | 0.754 | 0.125 | 45.8 | 28.3 | 83.3 | 1.4 |
| | Ragweed | 2.198 | 0.125 | 15.0 | 6.7 | 29.2 | 1.4 |
| glufosinate | Crabgrass | 0.151 | 0.125 | 83.3 | 20.0 | 75.0 | 0.9 |
| (bialaphos) | Ragweed | 0.194 | 0.125 | 22.5 | 37.5 | 75.0 | 1.5 |
| mesotrione | Crabgrass | 0.24 | 0.125 | 62.5 | 24.2 | 75.0 | 1.1 |
| | Ragweed | 0.96 | 0.125 | 25.0 | 15.0 | 45.8 | 1.3 |

Example 12

To further describe the spectrum of pre-emergence activity, tests were conducted in laboratory and field conditions. In laboratory testing, 35 seeds were placed on a ring of blotter paper inside a 3 cm petri dish and supplied with 4 ml of MBI-005 (≤0.1 mg MBI-005/ml). Water was used as a negative control and oryzalin applied as a positive control. Petri dishes were randomly placed in a growth room at 25° C. and 50% RH. Treatments were replicated three times and germinated seeds were counted 7 and 14 days after application; water was added as necessary to maintain moisture levels inside each petri dish.

In field testing, field soil containing weed seeds were treated with 38.2 L MBI-005/ha at a spray volume of 280 L/ha using a CO2 sprayer with flat fan nozzles. Treatments, including water as the negative control and Gallery as the positive control, were replicated four times and applied twice at a four week interval. Treatments were evaluated visually as % cover and above-ground fresh weights per container were taken.

Results in Table 12 indicate broad spectrum activity on both annual grasses and broadleaves, as well as on some perennials. Field results showing control over an eight-day period also suggest soil residual activity.

a growth room at 25° C. and 50% RH, and watered as necessary. Treatments were replicated five times and evaluated at 7 and 14 days for visual % damage, with 0% indicating no damage and 100% indicating plant death.

In field testing, field soil containing weeds at the 1-5 leaf stage were treated with 38.2 L MBI-005/ha at a spray volume of 374 L/ha. Treatments, including water as the negative control and WeedBGon or Preen Broadleaf as the positive

TABLE 12

Pre-Emergent Effect of MBI-005. An (R) indicates an herbicide resistant population.

| Plant Category | Species (common name) | Species (scientific name) | Rating at 0.1 mg/ml | Test Scale (lab/field) |
| --- | --- | --- | --- | --- |
| Grass, annual | Crabgrass | Digitaria sanguinalis | ++++ | lab & field |
| | Bluegrass | Poa annua | ++++ | lab & field |
| | Barnyardgrass | Echinochloa crus-gali | ++++ | lab |
| | Late watergrass (R) | Echinochloa phyllopogon | ++++ | lab |
| | Canarygrass | Phalaris minior | ++++ | lab |
| | Bearded Sprangletop | Leptochloa fascicularis | ++++ | lab |
| | Bristlegrass/Foxtail | Setaria viridis | ++++ | lab |
| | Fall Panicum | Panicum dichotomiflorum | ++++ | lab |
| Grass, perennial | Ryegrass | Lolium perenne | ++++ | lab |
| Broadleaf, annual | Ragweed | Ambrosia artemisifolia | ++++ | lab |
| | Buckhorn plantain | Plantago lanceolata | ++++ | lab |
| | Mustard | Brassica juncea | ++++ | lab |
| | Lambsquarters | Chenopodium album | +++ | lab |
| | Black nightshade | Solanum nigrum | ++++ | lab |
| | Clover | Trifolium repens | ++++ | lab |
| | Horseweed (R) | Conyza canadensis | ++++ | lab |
| | Palmer pigweed (R) | Amaranthus palmerii | +++ | lab |
| | Chickweed | Stellaria media | ++++ | Field |
| | Eclipta | Eclipta alba | ++ | Field |
| | Bittercress | Cardamine hirsuta | +++ | Field |
| | Henbit | Lamimum amplexicaule | +++ | Field |
| | Common groundsel | Senecio vulgaris | ++++ | Field |
| | Velvetleaf | Abutilon theophrasti | ++ | Field |
| | Shepherd's purse | Capsella bursa-pastora | ++++ | Field |
| | Hairy galinsoga | Galinsoga ciliata | +++ | Field |
| | New Zealand moss | Sagina procumbens | ++++ | Field |
| | Marsh watercress | Rorippa islandica | ++++ | Field |
| | Flexuous bittercress | Cardamine flexuosa | ++ | Field |
| | Common yellow oxalis | Oxalis stricta | ++++ | Field |
| Broadleaf, perennial | Dandelion | Taraxacum oficinale | ++++ | Field |

Key-Table 12A
Reduction of Germination (%) Rating

| Reduction of Germination (%) | Rating |
| --- | --- |
| 0-59 | + |
| 60-84 | ++ |
| 85-94 | +++ |
| 95-100 | ++++ |

Example 13

Further Studies on the Post-Emergent Effect of MBI-005

To further describe the spectrum of post-emergence activity, tests were conducted in laboratory and field conditions. For laboratory testing, 3-10 plants (depending on the species) at the 1-2 leaf stage plants in 2.5 cm square pots containing Sunshine Mix No. 2 planting media were sprayed at 1 mg MBI-005/mL at a rate of 40 gal/A using a cabinet track sprayer. Negative controls were sprayed with water and positive controls with glufosinate. Pots were randomly placed in control, were replicated four times and applied twice at a four week interval. The positive control on Late watergrass, Ricefield Bulrush, Smallflower sedge and Arrowhead was an herbicide containing as active ingredient 2,4-D and an organosilicone surfactant was added to MBI-005. Treatments were assessed for % control and % ground cover.

Results, shown in Table 13, indicate good (between 80 and 100% control) post-emergence activity on annual many broadleaves and sedges, and limited post-emergent activity on annual grasses, unless surfactants are added. Post-emergent control of perennials was generally limited except for *Oxalis pes-caprae*.

TABLE 13

Post-Emergent Effect of MBI-005

| Plant Category | Species (common name) | Species (scientific name) | Rating at 1 mg/ml | Test Scale (Lab/Field) |
|---|---|---|---|---|
| Grass, annual | Late watergrass | Echinochloa phyllopogon | +++ | Field |
| | Bluegrass | Poa annua | ++ | Field |
| Sedge, annual | Smallflower | Cyperus difformis | ++++ | Field |
| | Ricefield bullrush | Scirpus mucronatus | ++++ | Field |
| Sedge, perennial | Yellow nutsedge | Cyperus esculentus | + | Lab |
| Broadleaf, annual | Redstem filaree | Erodium cicutarium | ++ | Lab |
| | Mustard | Brassica juncea | ++++ | Lab |
| | Lambsquarters | Chenopodium album | +++ | Lab |
| | Arrowhead | Sagittaria montevidensis | ++++ | Field |
| | Velvetleaf | Abutilon theophrasti | ++ | Field |
| | Shepherd's purse | Capsella bursa-pastoris | ++++ | Field |
| | Hairy galinsoga | Galinsoga ciliata | +++ | Field |
| | Nightshade, Eastern Black | Solanum ptychanthum | ++ | Field |
| | Common yellow oxalis | Oxalis pes-caprae | ++++ | Field |
| | Clover | Trifolium hirtum | ++ | Field |
| | Sunflower | Helianthus anuus | ++ | Lab |
| | Mallow | Malva parviflora | + | Lab |
| | Common chickweed | Stellaria media | ++ | Field |
| | Eclipta | Eclipta alba | ++ | Field |
| | Hairy bittercress | Cardamine hirsuta | ++ | Field |
| | Henbit | Lamimum amplexicaule | ++++ | Field |
| | Common groundsel | Senecio vulgaris | ++++ | Field |
| | Marsh watercress | Rorippa islandica | ++ | Field |
| | Flexuous bittercress | Cardamine flexuosa | ++ | Field |
| Broadleaf, perennial | Dandelion | Taraxacum oficinale | ++ | Lab |
| | Bindweed | Convolvulus arvensis | + | Lab |
| | Bermuda buttercup | Oxalis pes-caprae | ++++ | Field |

Key-Table 13A

| Rating | Post-Emergence % control |
|---|---|
| + | 0-50 |
| ++ | 51-80 |
| +++ | 81-90 |
| ++++ | 91-100 |

Example 14

Synergistic Effect of MBI-005+Manuka Oil on the Emergence of Crabgrass

Figure 2:
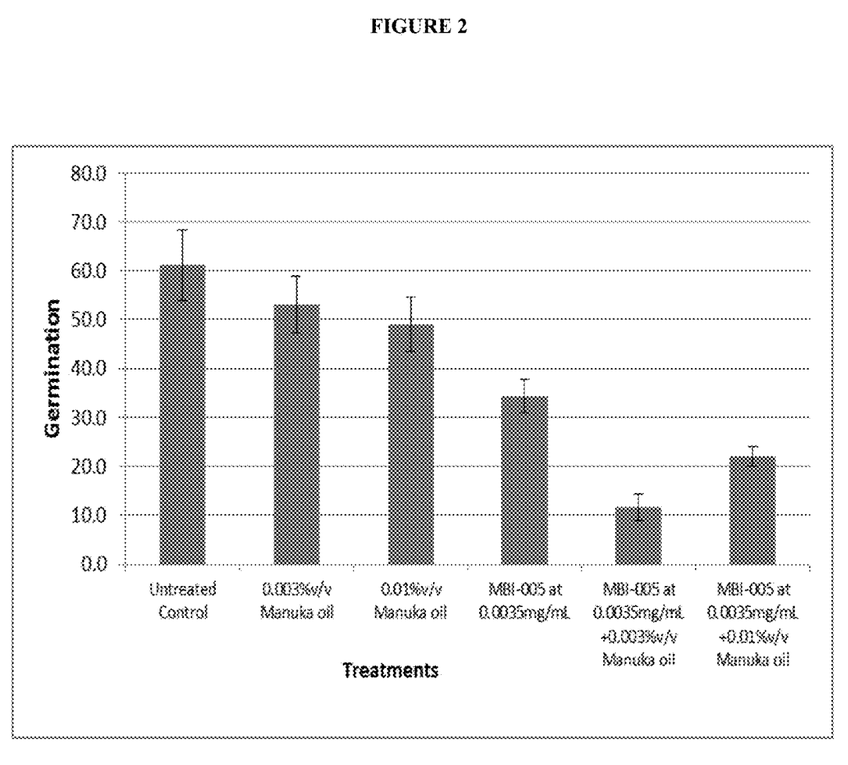
FIG. 2 shows the pre-emergent effect of MBI-005+ Manuka oil on crabgrass

Synergistic effects of MBI-005 and Manuka oil (containing leptospermone and other triketones) were evaluated on crabgrass seed germination in a laboratory experiment. Thirty-five seeds were placed on a ring of blotter paper inside a 3 cm petri dish, covered with 10 cm³ of inert baked clay particle media and supplied with 7 ml of 0.035 mg/ml MBI-005, a Manuka oil concentration, or a combination of MBI-005 and Manuka oil (FIG. 2). Water was used as a negative control. Petri dishes were randomly placed in a growth room at 25° C. and 50% RH. Treatments were replicated three times and germinated seeds were counted 7 days after application; water was added as necessary to maintain moisture levels inside each petri dish.

Synergy occurred between MBI-005 and Manuka oil at 0.003%v/v. Mild synergy was seen between MBI-005 and Manuka oil at 0.01%v/v. Synergy was calculated as the ratio of observed (E) to expected (E/Ee) reduction in germination using Colby's formula. Results are shown in FIG. 2

Example 15

005+m-Tyrosine Pre-Emergent Synergies in Crabgrass

Synergistic effects of MBI-005 and m-Tyrosine were evaluated on crabgrass seed germination in a laboratory experiment. Forty-five seeds were placed on a ring of blotter paper inside a 3 cm petri dish, covered with 10 cm³ of inert baked clay particle media and supplied with 7 ml of 0.035 mg/ml MBI-005, a m-Tyrosine concentration, or a combination of MBI-005 and m-Tyrosine (Table 14). Water was used as a negative control. Petri dishes were randomly placed in a growth room at 25° C. and 50% RH. Treatments were replicated three times and germinated seeds were counted 7 days after application; water was added as necessary to maintain moisture levels inside each petri dish.

Synergy occurred between MBI-005 and m-Tyrosine at 0.44 mg/mL but not for MBI-005 and m-Tyrosine at 22 mg/mL. Synergy was calculated as the ratio of observed (E) to expected (E/Ee) reduction in germination using Colby's formula.

TABLE 14

005 + m-Tyrosine Pre-Emergent Synergies in Crabgrass (7 DAT)

| Treatment | Description | AVG No. germinated | SE | E (% controlled compared to UTC) | Ee (expected control) | E/Ee |
|---|---|---|---|---|---|---|
| 1 | Untreated control | 44.3 | .9 | 0.0 | — | — |
| 2 | .22 mg/mL M-tyrosine | 40.7 | 2.6 | 8.3 | — | — |
| 3 | .44 mg/mL M-tyrosine | 44.0 | 3.8 | 0.8 | — | — |
| 4 | MBI-005 at 0.0035 mg/mL | 38.0 | 4.0 | 14.3 | — | — |
| 5 | MBI-005 at 0.0035 mg/mL + .22 mg/mL M-tyrosine | 35.0 | 2.1 | 21.1 | 21.4 | 1.0 |
| 6 | MBI-005 at 0.0035 mg/mL + .44 ml/mL M-tyrosine | 26.0 | 2.1 | 41.4 | 14.9 | 2.8 |

Example 16

MBI-005+Chelated Fe Post-Emergent Synergistic Effect in Crabgrass

Post-emergent synergistic effects of MBI-005 and Chelated iron were evaluated on crabgrass at the 1-2 leaf stage in a laboratory experiment. Ten seedlings in 2.5 cm square pots containing plant growth mix were sprayed with two suboptimal rates of MBI-005, 14.49 mg/mL of Chelated Fe, or a combination thereof, at a volume of 40 gal/A using a cabinet track sprayer. Negative controls were sprayed with water. Pots were randomly placed in a growth room at 25° C. and 50% RH, and watered as necessary. Treatments were replicated five times and evaluated at 7 and 15 days for visual % damage, with 0% indicating no damage and 100% indicating plant death.

A substantial synergistic effect occurred between MBI-005 and chelated Fe, at both concentrations of MBI-005. Synergy was calculated as the ratio of observed (E) to expected (E/Ee) percent control using Colby's formula.

TABLE 15

MBI-005 + Chelated Fe Post-Emergent Synergies in Crabgrass (15 DAT)

| | Crabgrass (15 DAT) | | | |
|---|---|---|---|---|
| Description | AVG E | STD DEV | Ee | E/Ee |
| Untreated Control | 0.0 | 0.0 | — | — |
| 12.5% MBI-005 (0.125 mg/mL) | 1.3 | 2.5 | — | — |
| 25% MBI-005 (0.25 mg/mL) | 1.3 | 2.5 | — | — |
| 95% Chelated Fe Field Rate (14.49 mg/ml) | 6.3 | 2.5 | — | — |
| 12.5% MBI-005 (0.125 mg/mL)/95% Chelated Fe | 25.0 | 0.0 | 7.4 | 3.4 |
| 25% MBI-005 (.25 mg/mL)/95% Chelated Fe | 25.0 | 0.0 | 7.4 | 3.4 |

Example 17

MBI-005+Atrazine Post-Emergent Synergies in Crabgrass (7 and 14 DAT)

Post-emergent synergistic effects of MBI-005 and Atrazine were evaluated on crabgrass at the 1-2 leaf stage in a laboratory experiment. Ten seedlings in 2.5 cm square pots containing plant growth mix were sprayed with two suboptimal rates of MBI-005, and 35% of the atrazine label rate (0.3 gallons/A), or a combination thereof, at a volume of 40 gal/A using a cabinet track sprayer. Negative controls were sprayed with water. Pots were randomly placed in a growth room at 25° C. and 50% RH, and watered as necessary. Treatments were replicated five times and evaluated at 7 and 14 days for visual % damage, with 0% indicating no damage and 100% indicating plant death.

A substantial synergistic effect occurred between MBI-005 and atrazine, at either concentration of MBI-005 at both 7 and 14 days after treatment. Synergy was calculated as the ratio of observed (E) to expected (E/Ee) percent control using Colby's formula.

TABLE 16

MBI-005 + Atrazine Post-Emergent Synergies in Crabgrass (7 and 14 DAT)

| | 7DAT Crabgrass | | | 14DAT Crabgrass | | |
|---|---|---|---|---|---|---|
| Description | AVG E | STD DEV | Ee | AVG/E | STD DEV | E/Ee |
| Untreated Control | 0.0 | 0.0 | — | 0.0 | 0.0 | — |
| 12.5% MBI-005 Label Rate (0.125 mg/mL) | 10.0 | 0.0 | — | 10.0 | 0.0 | — |
| 25% MBI-005 Label Rate (0.25 mg/mL) | 11.9 | 3.8 | — | 11.9 | 3.8 | — |
| 35% Atrazine Label Rate | 11.9 | 3.8 | — | 8.8 | 2.5 | — |
| 12.5% MBI-005/35% Atrazine | 65.6 | 12.0 | 3.2 | 78.1 | 12.0 | 4.4 |
| 25% MBI-005/35% Atrazine | 75.0 | 0.0 | 3.4 | 90.6 | 6.3 | 4.6 |

Example 18

Post-Emergent Effect of MBI-005+Rice Herbicides in Barnyard Grass

Post-emergent synergistic effects of MBI-005 and three common rice herbicides were evaluated on barnyard grass at the 1-2 leaf stage in a laboratory experiment. Ten seedlings in 2.5 cm square pots containing plant growth mix were sprayed to full coverage using a hand sprayer. Negative controls were sprayed with water. Pots were randomly placed in a growth room at 25° C. and 50% RH, and watered as necessary. Treatments were replicated three times and evaluated at 7 and 14 days for visual % damage, with 0% indicating no damage and 100% indicating plant death.

Synergistic effect were noted between MBI-005 and all three rice herbicides, 14 days after treatment. Synergy was calculated as the ratio of observed (E) to expected (E/Ee) percent control using Colby's formula.

TABLE 17

Post-Emergent Effect of MBI-005 + Rice Herbicides in Barnyard Grass

| Chemical Active Ingredient (AI) | % v/v of label rate (AI) | % of the label rate MBI 005 | % control chemical AI | % control MBI-005 | % control MBI-005 + chemical AI | Synergy coefficient |
|---|---|---|---|---|---|---|
| Clomazone | 13.3 | 25% | 37.50 | 28.30 | 91.66 | 1.66 |
| Penoxsulam | 13.0 | 12.5% | 25.0 | 17.5 | 75.0 | 1.97 |
| Bispyribac-sodium | 13.3 | 25% | 6.7 | 41.7 | 83.3 | 1.83 |

Example 19

Post-Emergent Effect of MBI-005+Rice Herbicides in Smallflower Umbrella Sedge Post-emergent synergistic effects of MBI-005 and five common rice herbicides were evaluated on small flower umbrella sedge at the 0.5-1 leaf stage in a laboratory experiment. Twenty seedlings in 2.5 cm square pots containing plant growth mix were sprayed to full coverage using a hand sprayer. Negative controls were sprayed with water. Pots were randomly placed in a growth room at 25° C. and 50% RH, and watered as necessary. Treatments were replicated three times and evaluated at 7 and 14 days for visual % damage, with 0% indicating no damage and 100% indicating plant death.

Synergistic effects were noted 14 days after treatment between MBI-005 and all three rice herbicides, with clomazone showing the greatest synergism with MBI-005. Synergy was calculated as the ratio of observed (E) to expected (E/Ee) percent control using Colby's formula.

TABLE 18

Post-Emergent Effect of MBI-005 + Rice Herbicides in Smallflower Umbrella Sedge

| Chemical Active Ingredient (AI) | % v/v of label rate AI | % of the label rate MBI 005 | % control AI | % control MBI-005 | % control MBI-005 + chemical AI | Synergy coefficient |
|---|---|---|---|---|---|---|
| Clomazone | 13% | 2.0% | 0.0 | 20.0 | 70.8 | 3.54 |
| Penoxsulam | 13% | 2.0% | 33.3 | 20.0 | 66.7 | 1.43 |
| Bispyribac-sodium | 13.3% | 0.5% | 37.5 | 3.3 | 62.5 | 1.57 |
| Thiobencarb | 25% | 2.0% | 41.7 | 20.0 | 83.3 | 1.56 |
| Propanil | .5% | 2.0% | 62.5 | 20.0 | 83.3 | 1.19 |

Example 20

Post-Emergent Effect of MBI-005+Propanil on Barnyard Grass

Post-emergent synergistic effects of MBI-005 and the common rice herbicide Propanil were evaluated on barnyard grass at the 1-2 leaf stage in a laboratory experiment. Ten seedlings in 2.5 cm square pots containing plant growth mix planting media were sprayed with 12.5% or 25% of the label rate of MBI-005, 25% of the propanil label rate, or a combination thereof, to full coverage using a hand sprayer. Negative controls were sprayed with water. Pots were randomly placed in a growth room at 25° C. and 50% RH, and watered as necessary. Treatments were replicated three times and evaluated at 7 and 14 days for visual % damage, with 0% indicating no damage and 100% indicating plant death.

Synergistic effects were noted between both rates of MBI-005 and propnail, 14 days after treatment. Synergy was calculated as the ratio of observed (E) to expected (E/Ee) percent control using Colby's formula.

TABLE 19

Post-Emergent Effect of MBI-005 + Propanil on Barnyard Grass

| Treatment Description | Observed Average % Efficacy (E) | Ee | E/Ee |
|---|---|---|---|
| UTC (No spray) | 0.0 | | |
| 12.5% MBI-005 | 10.0 | | |
| 25% MBI-005 | 20.0 | | |
| 25% Propanil | 32.5 | | |
| 250% Propanil + 12.5% MBI-005 | 79.2 | 39.25 | 2.02 |
| 25% Propanil + 25% MBI-005 | 75.0 | 46.00 | 1.63 |

Example 21

Post-Emergent Effect of MBI-005+Thiobencarb on Smallflower Umbrella Sedge

Post-emergent synergistic effects of MBI-005 and the common rice herbicide thiobencarb are evaluated on Smallflower umbrella sedge at the 0.5-1 leaf stage in a laboratory experiment. Twenty seedlings in 2.5 cm square pots containing plant growth mix were sprayed with 0.5%, 1% or 2% of the label rate of MBI-005, 25% of the thiobencarb label rate, or a combination thereof, to full coverage using a hand sprayer. Negative controls were sprayed with water. Pots were randomly placed in a growth room at 25° C. and 50% RH, and watered as necessary. Treatments were replicated three times and evaluated at 7 and 14 days for visual % damage, with 0% indicating no damage and 100% indicating plant death.

Synergistic effects were observed for three of the four thiobencarb+MBI-005 combinations, 14 days after treatment. Synergy was calculated as the ratio of observed (E) to expected (E/Ee) percent control using Colby's formula.

TABLE 20

005 + Thiobencarb Post-Emergent Synergies on Smallflower sedge

| Treatment Description | Observed Average % Efficacy (E) | Ee | E/Ee |
|---|---|---|---|
| UTC (No spray) | 0.0 | | |
| .5% MBI-005 | 3.3 | | |
| 2% MBI-005 | 20. | | |
| 25% Thiobencarb | 41.7 | | |
| 25% Thiobencarb + .5% MBI-005 | 62.5 | 43.61 | 1.43 |
| 25% Thiobencarb + 2% MBI-005 | 83.3 | 53.33 | 1.56 |
| UTC (No Spray) | 0.0 | | |
| 1% MBI-005 | 10.0 | | |
| 2% MBI-005 | 79.2 | | |
| 15% Thiobencarb | 25.0 | | |
| 15% Thiobencarb + 1% MBI-005 | 66.7 | 32.50 | 2.05 |
| 15% Thiobencarb + 2% MBI-005 | 79.2 | 84.38 | 0.94 |

Although this invention has been described with reference to specific embodiments, the details thereof are not to be construed as limiting, as it is obvious that one can use various equivalents, changes and modifications and still be within the scope of the present invention.

Various references are cited throughout this specification, each of which is incorporated herein by reference in its entirety.

Cited References:

Beauséjour, J., C. Goyer, et al. (1999). "Production of thaxtomin A by *Streptomyces scabies* strains in plant extract containing media." *Can J Microbiol* 45: 764-768.

Duke, S. O., S. R. Baerson, et al. (2003). "United States Department of Agriculture-Agricultural Research Service research on natural products for pest management." *Pest Manag Sci* 59: 708-717.

Duke, S. O., F. E. Dayan, et al. (2000). "Natural products as sources of herbicides: current status and future trends." *Weed Research* 40: 99-111.

Fry, B. A. and R. Loxia (2002). "Thaxtomin A: Evidence for a plant cell wall target." *Physiological and Molecular Plant Pathology* 60: 1-8.

Gerwick, B. C., P. R. Graupner, et al. (2005). Methylidene mevalonates and their use as herbicides. U. p. 7393812: 16.

Healy, F. G., M. J. Wach, et al. (2000). "The txtAB genes of the plant pathogen Streptomyces acidiscabies encode a peptidesynthetase required for phytotoxin thaxtomin A prodcution and pathogenicity." *Molecular Microbiology* 38: 794-804.

Hiltunen, L. H., I. Laakso, et al. (2006). "Influence of thaxtomins in different combinations and concentrations on growth of micropropagated potato shoot cultures." *J Agric Food Chem* 54: 3372-3379.

Hoagland, R. E. (2001). "Microbial allelochemicals and pathogens as bioherbicidal agents." *Weed Technology* 15: 835-857.

Kang, Y., S. Semones, et al. (2008). Methods of controlling algae with thaxtomin and thaxtomin compositions. USA, Novozymes Biologicals, Inc.

King, R. R., C. H. Lawrence, et al. (1992). "Chemistry of phytotoxins associated with *Streptomyces scabies*, the causal organism of potato common scab." *J. Agric. Food Chem* 40: 834-837.

King, R. R., C. H. Lawrence, et al. (1989). "Isolation and characterization of phytotoxin associated with *Streptomyces scabies*." *Journal of the Chemical Society, Chemical Communications* 13: 849-850.

King, R. R., C. H. Lawrence, et al. (2003). "More chemistry of the thaxtomin phytotoxins." *Phytochemistry* 64: 1091-1096.

King, R. R., C. H. Lawrence, et al. (2001). "Herbicidal properties of the thaxtomin group of phytotoxins." *J Agric Food Chem* 49: 2298-2301.

Loxia, R., R. A. Bukhalid, et al. (1995). "Differential production of thaxtomins by pathogenic *Streptomyces* species in vitro" *Phytopathology* 85: 537-541.

What is claimed is

1. A synergistic herbicidal composition comprising two herbicides having a synergistic effect, wherein
   a first herbicide is thaxtomin having a concentration of from 0.01 to 5.0 mg/ml and
   a second herbicide is atrazine having a concentration of from 0.01 to 50 mg/ml.

2. The combination according to claim 1, wherein said thaxtomin has the following composition:

wherein $R_1$ is methyl or H, $R_2$ is hydroxy or H, $R_3$ is methyl or H, $R_4$ is hydroxy or H, $R_5$ is hydroxy or H, $R_6$ is hydroxy or H, and combinations thereof.

3. The composition according to claim 1, wherein said thaxtomin has a concentration of between 0.2-0.4 mg/ml.

4. The composition according to claim 1, wherein said thaxtomin has a concentration of between 0.3-0.4 mg/ml.

5. A method for using the synergistic herbicidal composition according to claim 1, comprising applying the synergistic composition to a weed.

6. A method for modulating growth of monocotyledonous, dicotyledonous and sedge weeds and aquatic weeds selected from the group consisting of *Ammania* sp., Alisma plantago-aquatica, *Cyperus* sp., and *Leptochloa* sp., comprising applying to said weeds or soil a synergistic herbicidal composition comprising two herbicides having a synergistic effect, wherein a first herbicide is thaxtomin having a concentration of from 0.01 to 5.0 mg/ml and
   a second herbicide is atrazine having a concentration of from 0.01 to 50 mg/ml.

7. The method according to claim 6, wherein the weed is selected from the group consisting of *Chenopodium* sp., *Abutilon* sp., *Helianthus* sp., *Ambrosia* sp., *Amaranthus* sp., *Convolvulus* sp., *Brassica* sp., *Taraxacum* sp., *Solanum* sp., *Malva* sp., *Setaria* sp., *Bromus* sp., *Poa* sp., *Lolium* sp., *Festuca* sp., *Echinochloa* sp., *Cyperus* sp., *Scirpus* sp., *Erodium* sp., *Sagittaria* sp., *Capsella* sp., *Galinsoga* sp., *Oxalis* sp., *Trifolium* sp., *Stellaria* sp., *Eclipta* sp., *Cardamine* sp., *Lamium* sp., *Senecio* sp., and *Rorippa* sp.

8. The method according to claim 6, wherein the weed is selected from the group consisting of *Echinochloa phyllopogon, Poa annua, Cyperus difformis, Scirpus mucronatus, Cyperus esculentus, Erodium cicutarium, Brassica juncea, Chenopodium album, Sagittaria montevidensis, Abutilon* theophrasti, Capsella bursa-pastoris, Galinsoga ciliata, Solanum ptychanthum, Oxalis pes-caprae, Trifolium hirtum, Helianthus annuus, Malva parviflora, Stellaria media, Convolvulus arvensis, Eclipta alba, Cardamine hirsuta, Lamium amplexicaule, Senecio vulgaris, Rorippa islandica, Cardamine flexuosa, and Taraxacum officinale.

9. The method according to claim 6, wherein said monocotyledonous, dicotyledonous and sedge weeds are modulated in a cereal growth system.

10. The method according to claim 6, wherein the cereal growth system is a rice growth system.

* * * * *